(12) United States Patent
Dodabalapur et al.

(10) Patent No.: US 7,538,538 B2
(45) Date of Patent: May 26, 2009

(54) METHOD OF USING A FOUR TERMINAL HYBRID SILICON/ORGANIC FIELD EFFECT SENSOR DEVICE

(75) Inventors: Ananth Dodabalapur, Austin, TX (US);
Deepak Sharma, Austin, TX (US);
Daniel Fine, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/133,795

(22) Filed: Jun. 5, 2008

(65) Prior Publication Data

US 2008/0278140 A1    Nov. 13, 2008

Related U.S. Application Data

(62) Division of application No. 11/291,729, filed on Dec. 1, 2005, now Pat. No. 7,397,072.

(51) Int. Cl.
*H01L 23/58* (2006.01)
(52) U.S. Cl. ................ 324/71.5; 324/769; 257/40
(58) Field of Classification Search ........... 234/71.5, 234/769, 765; 257/40
See application file for complete search history.

(56) References Cited

U.S. PATENT DOCUMENTS

| | | | | |
|---|---|---|---|---|
| 5,369,295 | A | 11/1994 | Vinal | 257/288 |
| 5,612,228 | A | 3/1997 | Shieh et al. | 438/99 |
| 5,625,199 | A | 4/1997 | Baumbach et al. | 257/40 |
| 5,885,876 | A | 3/1999 | Dennen | 438/294 |
| 5,946,551 | A | 8/1999 | Dimitrakopoulos et al. | 438/99 |
| 6,252,245 | B1 * | 6/2001 | Katz et al. | 257/40 |
| 6,278,127 | B1 | 8/2001 | Dodabalapur et al. | 257/40 |
| 6,484,559 | B2 | 11/2002 | Dodabalapur et al. | 73/23.34 |
| 6,528,816 | B1 | 3/2003 | Jackson et al. | 257/40 |
| 6,575,013 | B2 | 6/2003 | Bao et al. | 73/23.34 |

(Continued)

FOREIGN PATENT DOCUMENTS

DE    43 38 732 A1    5/1995

(Continued)

OTHER PUBLICATIONS

"Electroluminescence from single monolayers of nanocrystals in molecular organic devices," Seth Cole, et al., Nature Publishing Group, vol. 420, pp. 800-803 (2002).

(Continued)

*Primary Examiner*—Vincent Q Nguyen
(74) *Attorney, Agent, or Firm*—Winstead P.C.

(57) ABSTRACT

A four terminal field effect device comprises a silicon field effect device with a silicon N-type semiconductor channel and an N+ source and drain region. An insulator is deposited over the N-type semiconductor channel. An organic semiconductor material is deposited over the insulator gate forming a organic semiconductor channel and is exposed to the ambient environment. Drain and source electrodes are deposited and electrically couple to respective ends of the organic semiconductor channel. The two independent source electrodes and the two independent drain electrodes form the four terminals of the new field effect device. The organic semiconductor channel may be charged and discharged electrically and have its charge modified in response to chemicals in the ambient environment. The conductivity of silicon semiconductor channel is modulated by induced charges in the common gate in response to charges in the organic semiconductor channel.

6 Claims, 6 Drawing Sheets

U.S. PATENT DOCUMENTS

| | | | |
|---|---|---|---|
| 6,661,299 B2 | 12/2003 | Dodabalapur et al. | 331/57 |
| 6,946,865 B2 * | 9/2005 | Mizuno et al. | 324/765 |
| 7,241,652 B2 | 7/2007 | Park et al. | 438/197 |
| 2004/0012397 A1 * | 1/2004 | Mizuno et al. | 324/522 |
| 2005/0258422 A1 | 11/2005 | Koo et al. | 527/59 |
| 2008/0087883 A1 * | 4/2008 | Suwa et al. | 257/40 |

OTHER PUBLICATIONS

"Nanowire Nanosensors for Highly Sensitive and Selective Detection of Biological and Chemical Species," Yi Cui, et al., Science, vol. 293, pp. 1289-1292 (2001).

"Response of a poly (pyrrole) resistive micro-bridge to ethanol vapour," J.W. Gardner, et al., Elsevier Sceince, vol. 0925-4005, pp. 289-295 (1998).

"Flexible active-matrix displays and shift registers based on solution-processed organic transistors," Gerwin H. Gelinck, et al., Nature Publishing Group, vol. 3, pp. 106-110 (2004).

"Nanoscale Morphology of Conjugated Polymer/Fullerence-Based Bulk-Heterojunction Solar Cells," Harald Hoppe, et al., Advanced Functional Materials, vol. 14, No. 10, pp. 1005-1011 (2004).

"Hybrid Nanorod-Polymer Solar Cells," Wendy U. Huynh, et al., Science, vol. 295, pp. 2425-2427 (2002).

"Organic-Inorganic Hybrid Materials as Semiconducting Channels in Thin-Film Field-Effect Transistors," C.R. Kagan, et al., Science, vol. 286, pp. 945-947 (1999).

"Control of carrier density by self-assembled monolayers in organic field-effect transistors," S. Kobayashi, et al., Nature Publishing Group, vol. 3, pp. 317-322 (2004).

"Stacked Pentacene Layer Organic Thin-Film Transistors with Improved Characteristics," Y.-Y. Lin, et al., IEEE Electron Device Letters, vol. 18, No. 12, pp. 606-608 (2007).

"Molecular Recognition by Self-Assembled Monolayers of Cavitand Receptors," K.D. Schierbaum, et al., Science, vol. 265 pp. 1413-1415 (1994).

"Analysis of Medication Off-odors Using an Electronic Nose," Susan S. Schiffman, et al., Oxford University Press, pp. 119-128 (1996).

"Organic thin-film transistor-driven polymer-dispersed liquid crystal displays on flexible polymeric substrates," C.D. Sheraw, et al., Applied Physics Letters, vol. 80, No. 6, pp. 1088-1090 (2002).

"Chemical Detection with a Single-Walled Carbon Nanotube Capacitor," E.S. Snow, et al., Science, vol. 307, pp. 1942-1945 (2005).

"Carrier transport and density of state distributions in pentacene transistors," A.R. Volkel, et al., The American Physical Society, vol. B 66 195336, pp. 1-8 (2002).

"Solid State Electronic Devices," Ben G. Streetman, et al., Prentice hall, Fifth Edition, ISBN 0-13 025538-6 (1972).

* cited by examiner

METHOD OF USING A FOUR TERMINAL HYBRID SILICON/ORGANIC FIELD EFFECT SENSOR DEVICE

CROSS REFERENCE TO RELATED APPLICATIONS

The present application is a divisional application of U.S. patent application Ser. No. 11/291,729, entitled "Structure for and Method of Using a Four Terminal Hybrid Silicon/Organic Field Effect Sensor Device," filed Dec. 1, 2005, now U.S. Pat. No. 7,397,072, which is incorporated by reference herein. The present application claims priority benefits to U.S. patent application Ser. No. 11/291,729 under 35 U.S.C. §121.

TECHNICAL FIELD

The present invention relates to hybrid composite silicon/organic field effect devices wherein the gate charge is induced by electrical as well as environmental elements.

BACKGROUND INFORMATION

The use of gas sensors and sensor arrays for odor analysis has attracted a great deal of attention in recent years. The principal goal of such research is to create a technology that can detect a wide range of odors with sufficient reproducibility, selectively, and stability to enable the construction of electronic noses that possess learning, storage, and recognition capabilities. Such systems are expected to be useful in a number of applications including food processing, environmental remediation, agriculture, and medical diagnostics. Organic transistors are being investigated for use in low cost flexible circuitry and in displays. It has been shown that organic transistors also make excellent gas sensors. The sensitivity of some organic transistors and a few gases has been noted in previous work. It is been shown that more information is available from a transistor sensor than an equivalent to chemiresistor sensor. It is an shown that field effect devices with active layers comprised of thin film of a conjugated small molecule, oligomer, or polymer, possess many of the required characteristics of gas sensors. It is been demonstrated that such devices are sensitive to a wide range of vapors at concentrations in the ppm range. The large variety of semiconductor materials available and the degrees of freedom available in modifying their molecular and morphological structures enable the construction of sensor arrays that could detect odors through pattern recognition.

The basic structure of the field effect sensor shown in FIG. 1(a) of "Electronic Sensing of Vapors with Organic Sensors" Applied Physics Letters, Volume 78, Number 15, Apr. 9, 2001. The field effect sensor consists of a thin film (of the order 10-100 nm) of an active semiconductor deposited by either a vacuum sublimation or solution-based techniques on dielectric-coated conductor. Gold electrodes are evaporated over the semiconductor with spacing of 200 um. The devices is biased so that the channel has a field-induced charge with densities in the range of $10^{12}$-$10^{13}$ cm$^{-2}$. The functioning of such field effect devices is described in the literature. Measurements were also made with zero gate bias. The morphology of semiconductor materials used in the study is polycrystalline with grain size in the 10-100 nm range.

While the organic transistors demonstrate a change in drain to source current when its semiconductor channel is exposed to selected gases, their sensitivity is low and it is difficult to "reset" the device by clearing out the trapped charges after an exposure to an analyte gas. Additionally, in previous work on organic FET sensors, the active organic transistor channel has a dual role: sensing as well as transduction. This dual role may cause reliability problems. Therefore there is a need for a new gas sensor device that uses a organic field effect transistor (FET) device combined with a silicon semiconductor field effect device that is more sensitive and has the ability to be electronically reset. There is also a need for a gas sensor device where the sensing takes place in the organic FET and transduction takes place in a parallel integrated silicon FET device.

SUMMARY OF THE INVENTION

A new four-terminal FET chemical sensor device is described that consists of two coupled channels: one comprising an organic or polymeric semiconductor and the second comprising silicon. The gates while common are not electrically connected to any external potential. The four terminals consist of source and drain terminals electrically coupled to the channel of the organic semiconductor and source and drain terminals electrically coupled t to the channel of the silicon semiconductor.

In one embodiment, the silicon device is fabricated on to a P-type substrate by diffusion of N+ material to form the source and drain regions and N$^-$ material to form the channel region. An insulator layer (e.g., $SiO_2$) is deposited over the N-channel of the silicon semiconductor. Next, a suitable semiconductor organic material is deposited on the insulator layer forming the channel of the organic field effect device. Source and drain contacts are deposited at each end of organic semiconductor channel. The source and drain contacts for the organic semiconductor channel are of a material type for making good electrical connection to the organic semiconductor material.

The two channels are coupled such that charges induced in one channel will modify the conduction of the other channel due to the common gate insulator layer. In one embodiment, the organic channel is exposed to air such that it is able to interact with chemicals in the ambient environment. This interaction enables the new four terminal device to have multiple modes of operation, the common gate region may be charged from chemicals interacting with the exposed organic channel, the organic channel may be electrically reset by applying appropriate potentials to its source and drain, the silicon semiconductor channel may be charged electrically to modify the organic channel, etc. In all cases, the conduction of the channels may be measured by monitoring current in the respective organic and silicon semiconductor channels before and after exposure to either environmental or electrical stimulus.

This four terminal field effect device of the present invention represents a major improvement over both the traditional CHEMFET which is a silicon MOSFET with the gate uncovered to be chemically sensitive and an organic transistor chemical sensor. While the four terminal field effect device of the present invention may also function as a traditional CHEMFET, one of the more powerful sensing modes occurs when the two channels are coupled and changes in the organic channel carrier density in response to analyte delivery are reflected as changes in the current through the silicon channel.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings in which.

DETAILED DESCRIPTION

Figure 1:
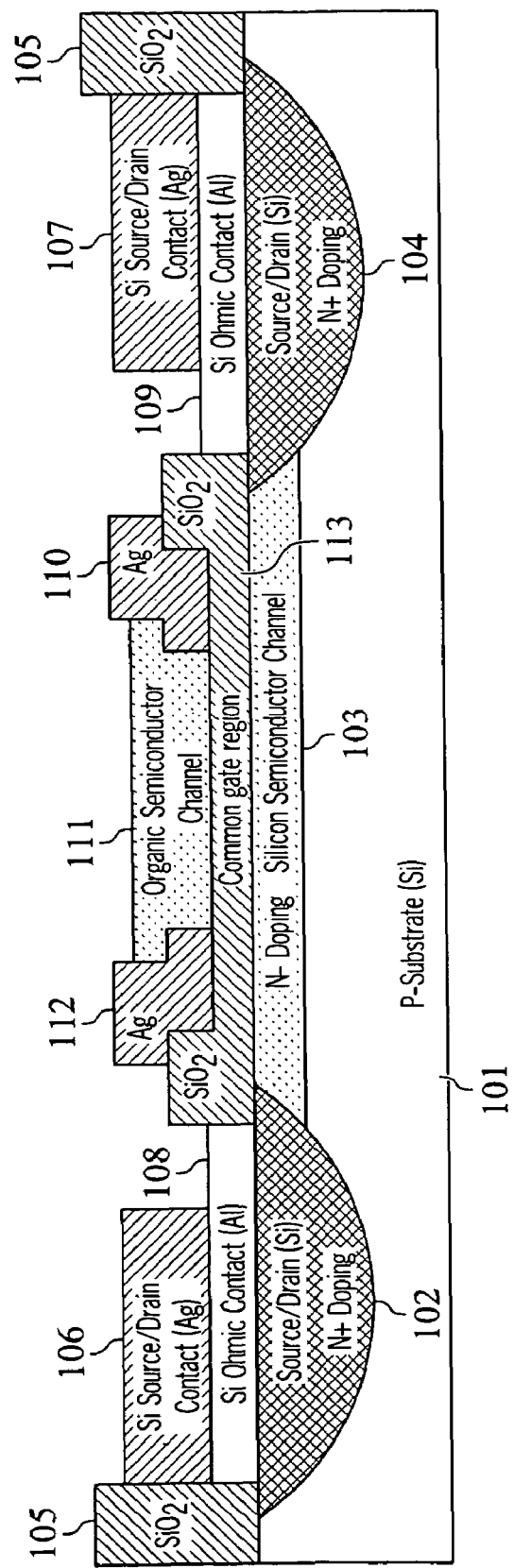
FIG. 1 is a cross-section view of a composite field effect device according to embodiments of the present invention.

In the following description, numerous specific details are set forth to provide a thorough understanding of the present invention. For example, specific details of certain semiconductor process steps. In other instances, well-known subsystems have been shown in block diagram form in order not to obscure the present invention in unnecessary detail.

Refer now to the drawings wherein depicted elements are not necessarily shown to scale and wherein like or similar elements are designated by the same reference numeral through the several views.

FIG. 1 is a cross-section view of a combination hybrid organic and silicon semiconductor FET device 100 according to embodiments of the present invention. The first step in device fabrication is to fabricate a silicon N-channel field effect transistor (NFET). Using photolithography and ion-implantation techniques, source 102 and drain 104 regions are patterned and doped with phosphorous in a P-type silicon substrate 101 (resistivity: 2-8 Ω-cm). The NFET is designed to be a depletion mode (normally on) device and the channel region 103 is doped with phosphorous realize a threshold voltage (VT) near zero volts. A thin (e.g., 40 nm thick) dielectric (e.g., $SiO_2$) forms the common gate region 113 and is thermally grown through a combination of wet and dry processes. Aluminum metal 108 and 109 electrodes are is sputtered on the source and drain regions 102 and 103 respectively of the NFET to form ohmic contacts. The source and drain electrodes are 102 and 103 then covered with a silver deposition 106 and 107 respectively using e-beam evaporation.

Organic semiconductor material is deposited over a portion of the common gate region 113 to form the channel 111 of an organic P-channel FET (PFET) device. The source and drain electrodes of the organic PFET device is then formed by depositing silver 110 and 112. The surface of channel 111 is exposed to the ambient environment 114. Source/drain electrodes 110 and 112 of the organic semiconductor PFET and 106 and 107 of the silicon semiconductor NFET may be electrically coupled to circuitry which enables different potentials to be applied for different modes of operation of the hybrid combination four terminal device 100.

In forming the organic PFET, hexamethyldisilazane (HMDS), which is a self-assembled monolayer (SAM), is first deposited on the $SiO_2$ gate region 113. Next, pentacene is deposited using vacuum deposition technique as the organic semiconductor channel 111. The SAM is used to improve the crystalline ordering of the pentacene on the $SiO_2$ gate region 113. If need be, an indium substrate contact (not shown) may be used to externally modify the threshold voltage through changing the bias on substrate 101. In experimental devices, three different channel lengths of 35 µm, 54 µm and 1 mm have been used for the silicon semiconductor NFET while keeping the channel 103 width to length (W/L) ratio equal to 5.

The combination hybrid organic and silicon semiconductor FET device 100 in FIG. 1 has four terminals, the source and drain terminals of the organic semiconductor PFET and the source and drain of the silicon semiconductor NFET. By applying various bias voltages to these terminals, the operation modes device 100 may be electrically changed while the common gate allows the organic PFET to modify the silicon NFET when its organic semiconductor channel is exposed to analyte. Likewise, the silicon semiconductor channel may be charged electrically and modify the response of the organic semiconductor channel to an analyte. Two of the most common modes of operation for device 100 is the Chemical Field Effect Transistor (CHEMFET) mode and the Chemical Memory Mode.

In the Chemical Memory Mode, the NFET is biased such that it is ON and the PFET is OFF. In this first step, the current in silicon semiconductor channel 100 is then measured. Next, both the NFET and the PFET are biased such that they are both ON, wherein the common gate region causes cross-gating between the two devices. At this step, the analyte (e.g., ethanol vapor) is delivered to the organic semiconductor (pentacene) channel. The analyte causes changes in the free carrier density in the PFET due to the interaction between the analyte and the pentacene layer which leads to hole trapping. Essentially, the analyte molecules polarized and the resultant dipoles are held by electrostatic attraction to the holes in the organic semiconductor channel 111. In the next step, the bias is removed such that the holes which are not trapped exit the organic semiconductor channel 111 while trapped holes remain and significantly alter current in silicon semiconductor channel 103. The current in silicon semiconductor channel 103 has been shown to increase as much as 65 times in experimental models. This increase comes from the charged holes trapped in the pentacene layer which create an accumulation of electrons in addition to the residual charges in the doped silicon channel. This increase can be described as an increase in current due to a decrease in the threshold voltage of the silicon NFET. Since the channel current has a well know exponential dependence on the difference between the gate to source voltage and the threshold voltage in the sub-threshold region, maximum change in channel current is expected in this sub-threshold region of operation.

The trapped holes in the organic semiconductor channel 111 can be released by reverse biasing the device for an extended time (e.g., 60 seconds), enabling the sensor device 100 to be electrically refreshed. The ability to electrically refresh the sensor device 100, according to embodiments of the present invention, is a major advantage over traditional CHEMFET sensors which often experience drift in their sensor characteristics with time due to inefficiencies in removing trapped charges/dipoles after a sensing event.

Figure 2A:
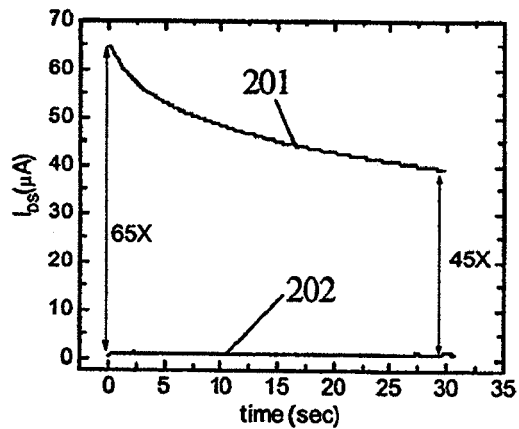
FIGS. 2A-2D illustrates drain to source current resulting from various operations of the field effect device of the present invention.

FIG. 2A illustrates the drain to source current through the silicon semiconductor channel 103 in the Chemical Memory Mode after the following steps. First, both the silicon NFET and the organic PFET are biased ON while the organic semiconductor channel 111 is exposed to an ethanol analyte. Secondly, the bias on the organic PFET is removed such that the holes which are not trapped exit the organic semiconductor channel 111. The trapped holes remain in organic semiconductor channel 111 and induce charge carriers, via the common gate region, in the silicon semiconductor channel 103 significantly increasing its channel current. As shown the channel current in the silicon semiconductor channel 103 increases by a factor of 65 before relaxing to a value of 45 in approximately 30 seconds.

Figure 2B:
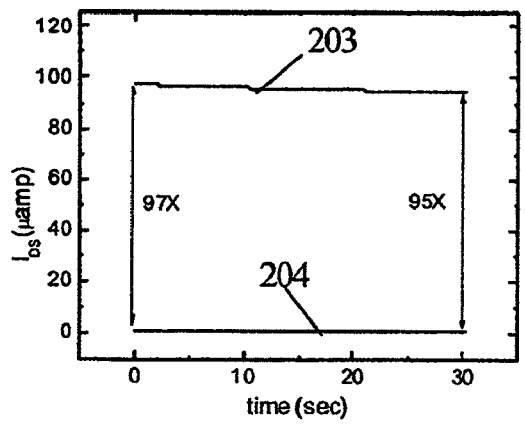

FIG. 2B illustrates the change in the silicon semiconductor channel 103 following the steps recited relative to FIG. 2A with the exception that the background environment is Nitrogen instead of air as was the case relative to FIG. 2A. In this case the silicon semiconductor channel current increased by a factor of 97 instead of 65 and the decay over time was less. The explanation for this is still under investigation.

Figure 2C:
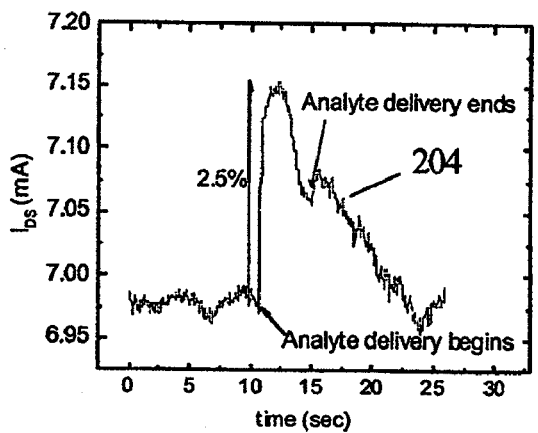

FIG. 2C illustrates measurements taken in the CHEMFET mode wherein the NFET is biased ON and the PFET is biased OFF. In this case, the NFET channel current increases only about 2.5% during ethanol analyte delivery. This change may be accounted for realizing that the polar nature of the ethanol analyte weakly interacts with the organic semiconductor P-type channel and induces accumulation of electrons in the silicon semiconductor N-type channel.

Figure 2D:
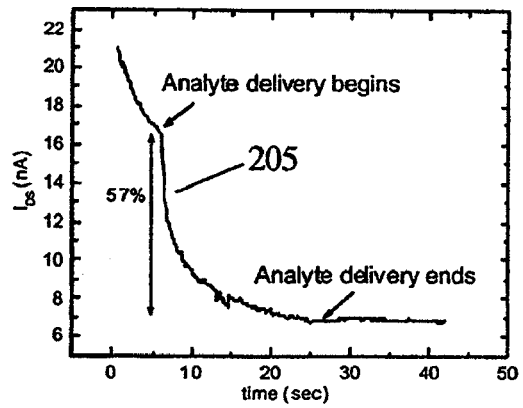

FIG. 2D illustrates the silicon semiconductor drain/source current ($I_{DS}$) in the organic thin film transistor (TFT) based sensing mode. In this mode, the silicon NFET is biased such that its $V_{Drain}$ and $V_{Source}$ are equal to zero volts and the organic PFET is biased ON. Upon ethanol analyte delivery, a measurement of the organic semiconductor channel current reveals that the current appreciably decreases by a factor of approximately two to one.

Figure 3B:
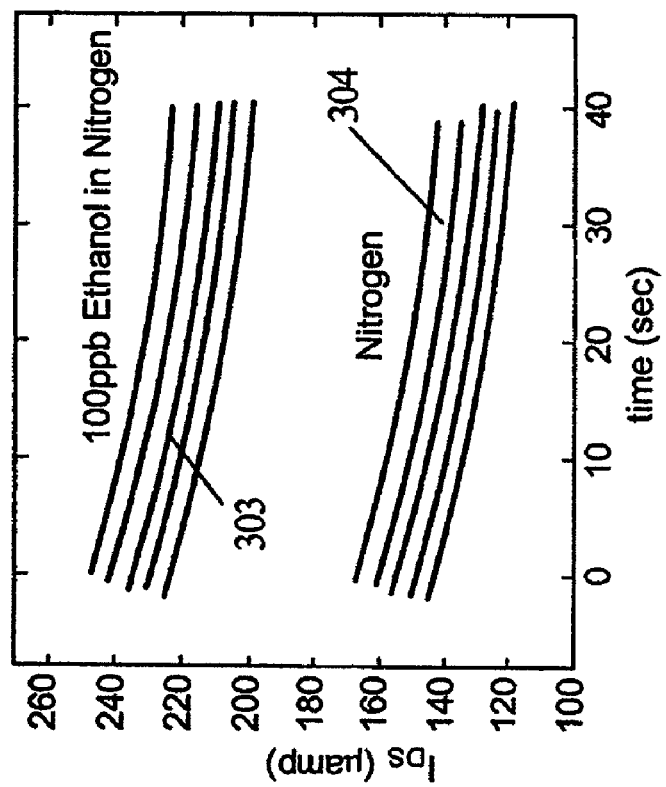
FIGS. 3A-3B illustrates drain to source current resulting from various operations the field effect device of the present invention.
Figure 3A:
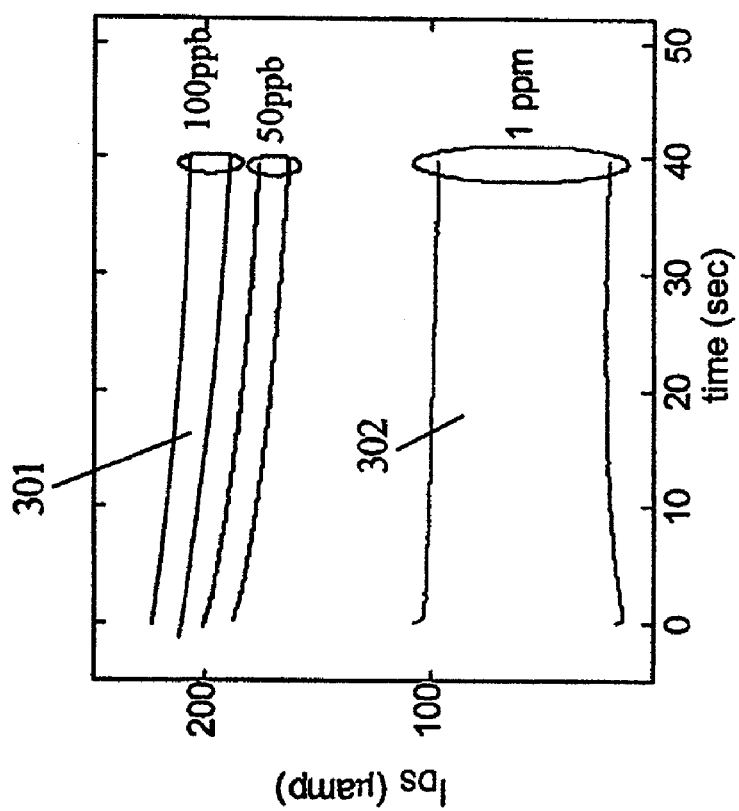

For measuring the absolute sensitivity of the device in the chemical memory mode, a second measurement set-up was used. A probe station which can be pumped down to less than $10^{-4}$ torr is connected with two high precision needle valves that can control the flow rate of any gas. Ethanol source is connected to one valve and the second valve is used to bleed in diluting gas (nitrogen or normal moist air) to further dilute the ethanol mixture. Gases are bled in at less than $10^{-4}$ torr pressure to reach 450 torr and the partial pressures are chosen to reach at a desired ppm/ppb level of ethanol. Before any measurements, the device is left to equilibrate with the ambient. First, the effect of both nitrogen and air diluting gases, treating each as analytes themselves, was measured in the Chemical Memory Mode. Subsequently, measurements with ethanol and diluting gas mixture were conducted. The measurements in diluting gas were subtracted from those of the ethanol mixed with the diluting gas to calculate the actual ethanol response. It was found that when Nitrogen is used as a diluting gas, the Minimum Detection Limit (MDL) of ethanol is 50 ppb, curves 301 in FIG. 3A. For statistical reliability, measurements in each kind of ambients were done for five times on the same device. These multiple measurements in ethanol mixed in Nitrogen and Nitrogen alone are plotted together as bands 303 and 304 respectively. It is evident in FIG. 3B that each measurement in the ethanol mix is widely separated from each measurement in Nitrogen. Although most of the literature available on sensitivity measurements describe measurements in controlled ambient such as nitrogen, dry air etc., it is important to know the effect of moisture present in air on the sensor performance. Thus, normal room air at 42% relative humidity is used as a diluting gas as well and the same measurements as described in above paragraph were repeated. The MDL of ethanol when mixed with air is 30 ppm. To further improve the MDL, receptors may be used to increase sensitivity.

Figure 4:
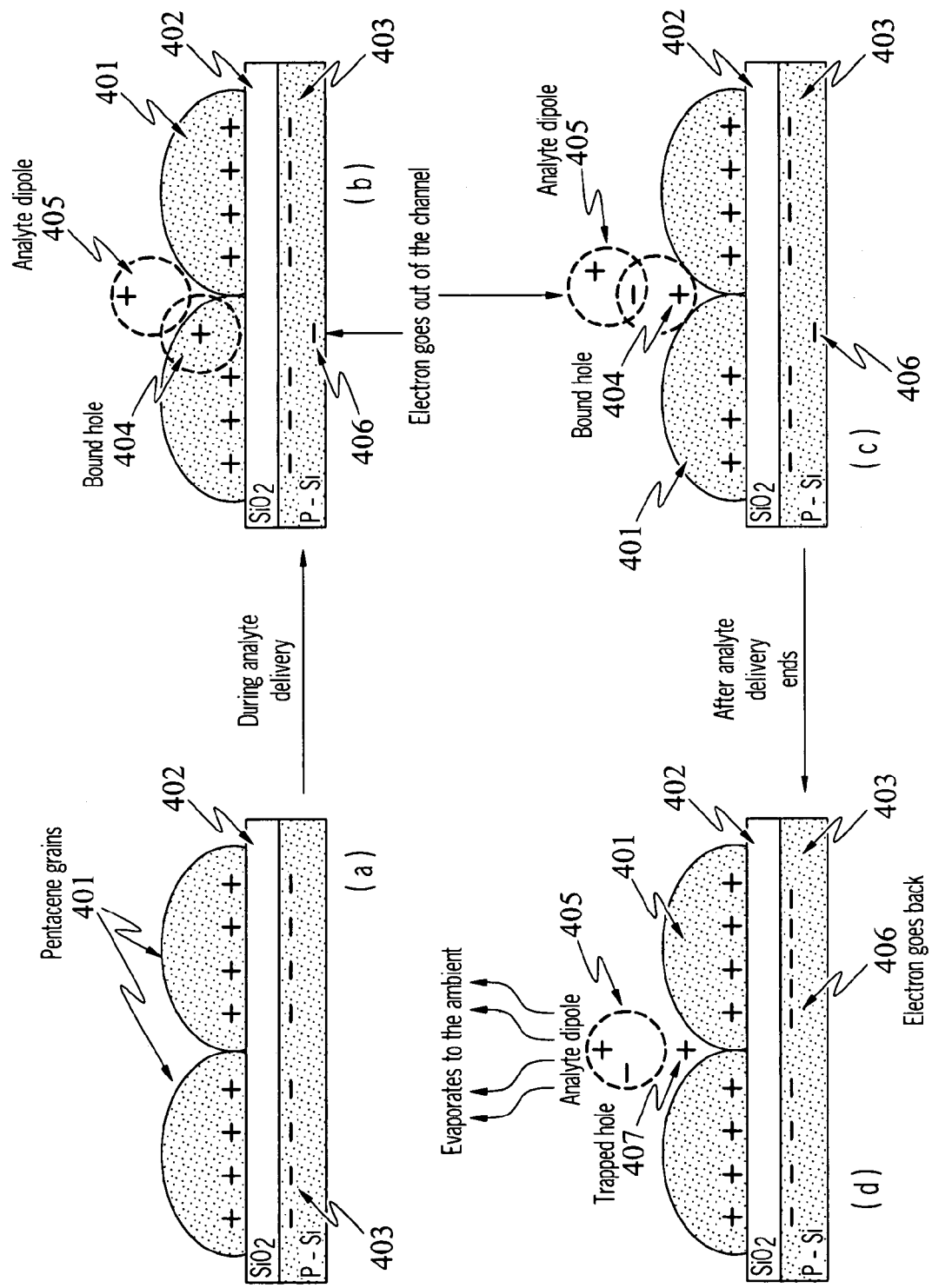
FIG. 4 illustrates charge distributions during and after analyte delivery to the field effect device of the present invention.

FIG. 4 shows a pictorial sequence illustrating the theory of operation of the composite 4 terminal organic/silicon field effect device according to embodiments of the present invention. The operation was determined from analysis of the CM mode, CHEMFET mode, and the organic TFT based sensor mode. For simplicity the silicon semiconductor channel is not outlined. In frame (a), pentacene grains 401 of the organic semiconductor channel are shown deposited on the common $SiO_2$ gate region over the silicon semiconductor channel 403. In frame (b), analyte is delivered to the organic semiconductor channel wherein the interaction between the analyte and the organic semiconductor channel is dependent on whether the PFET is biased ON or OFF. When the PFET is biased ON, holes in the P-channel are electrostatically coupled with the electrons 403 in the silicon semiconductor N-channel (not outlined). The dipoles present in the analyte bind some free holes in the organic semiconductor material 401 through columbic forces forming and exemplary bound hole 404. This binding between holes and analyte dipoles reduces coupling between holes and electrons in both the silicon semiconductor and the organic semiconductor channels and some electrons (e.g., exemplary electron 406 leave the silicon semiconductor channel as shown in frame (c). As soon as the analyte delivery ends, analyte molecules evaporate to the ambient because of weak coupling between polar analyte (alcohol) and non-polar organic layer (pentacene) leaving most of the holes in the deep traps. These trapped holes 407 again induce electrons (e.g., exemplary electron 406) into silicon semiconductor channel. These trapped holes, which were not present during the silicon channel current measurement before analyte delivery, induce additional electrons in the channel and increase the current after analyte delivery during the CM mode.

In the CHEMFET mode, the PFET is biased OFF upon analyte delivery. In this case, the dipoles have a weak interaction with the organic semiconductor which momentarily attracts them to the surface where they align themselves at the dielectric-organic interface such that their positive pole is coupled with the residual electrons in the N-channel and produces an increase in current as shown previously in FIG. 2C. When analyte delivery ends in the CHEMFET mode, the concentration of dipoles gets reduced as the analyte molecules leave the device surface and the silicon channel current returns to its initial charge distribution state.

Comparisons across different sensor platforms may be difficult owing to different test procedures used. However, it may be stated that the 4 terminal composite field effect device fabricated according to embodiments of the present invention and operated in the CM mode is 10-100 times more sensitive than an a traditional CHEMFET device. This difference in sensitivity results because in the traditional CHEMFET, it is dipoles attached to the gate that cause a charge perturbation in the FET channel whereas in the 4 terminal composite field effect device according to embodiments of the present invention, it is the unipolar charges that are trapped, as in a memory, that cause channel conductivity modulation. The modulation remains in effect until the trapped charges are released by an applied reverse bias.

Figure 5:
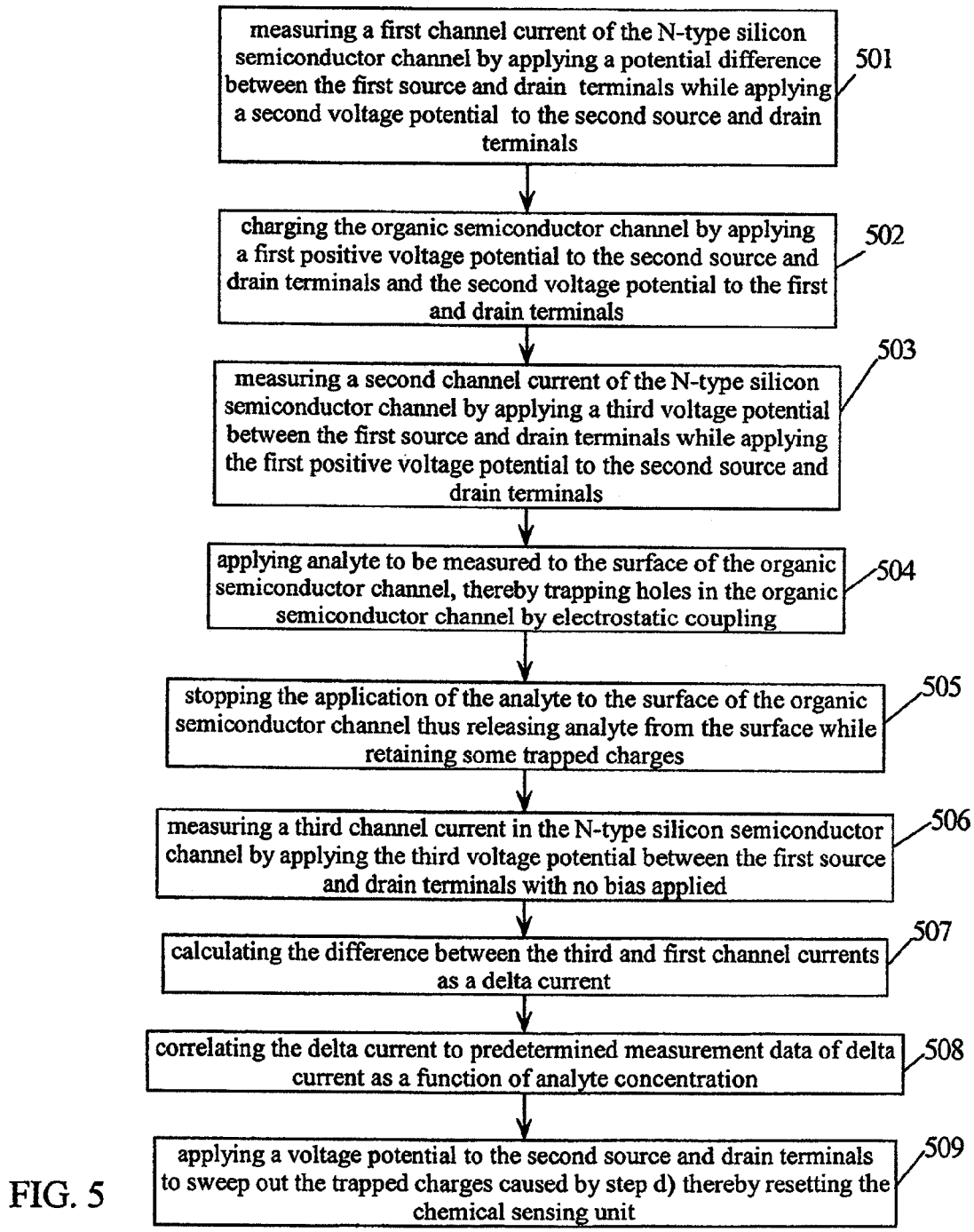
FIG. 5 a flow diagram of method steps used in another embodiment of the present invention.
Figure 6:
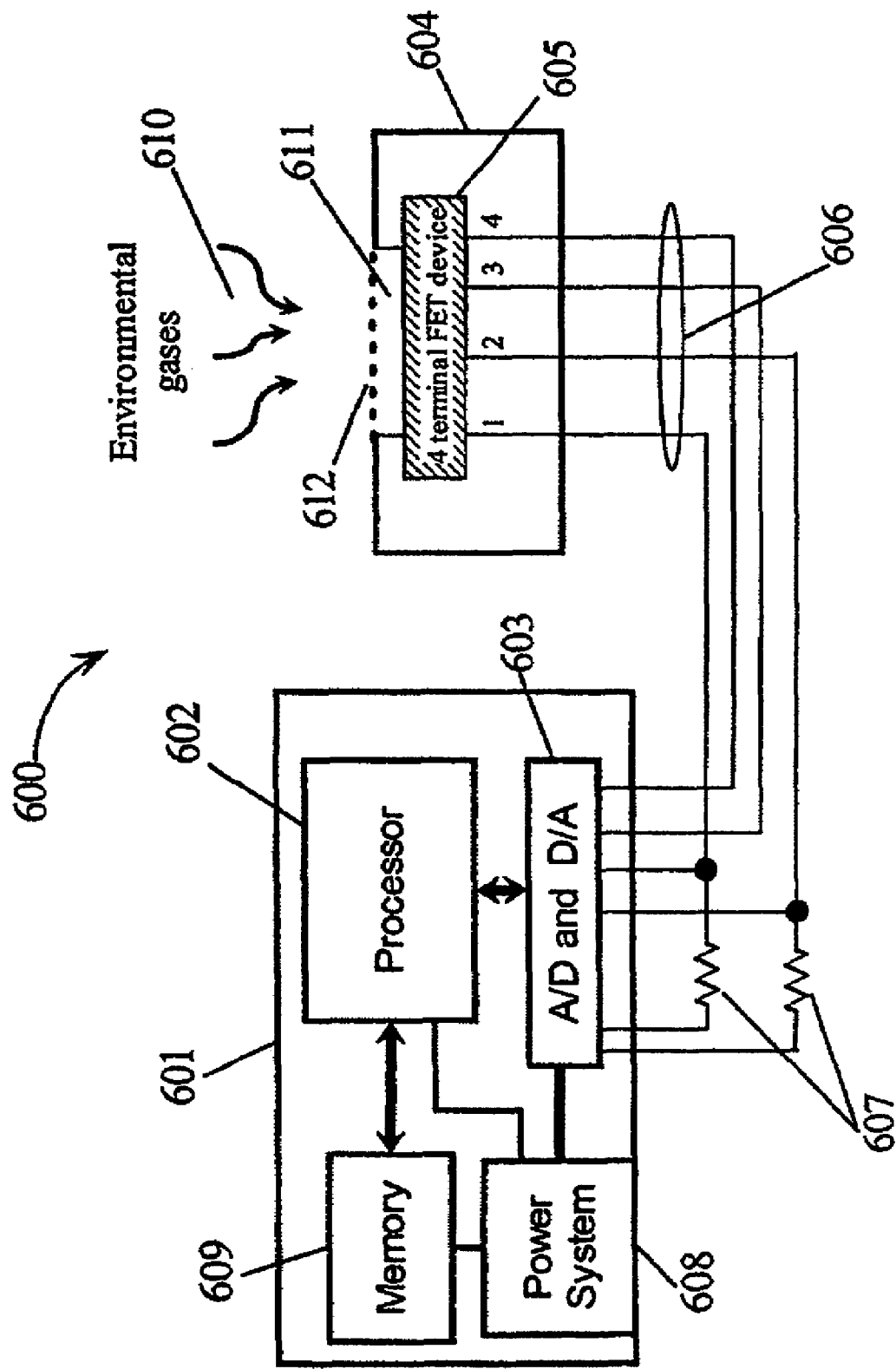
FIG. 6 is a block diagram of a sensor system suitable for practicing embodiments of the present invention.

FIG. 6 illustrates a sensor system 600 suitable for practicing embodiments of the present invention. A four terminal composite field effect device 605 is made according to embodiments of the present invention and may be operated in one of multiple modes. For example it may be operated in the CM mode whose steps are outlined in FIG. 5. Four terminal composite field effect device 605 may be housed in a sensor head 604 with an opening 611. Dotted line 612 illustrates a closure that may be used to seal device 605 from the environment during reset. The four terminals are wired (606) to control unit 601, where terminals 1 and 3 are coupled to the drain and source of the organic semiconductor device and terminals 2 and 4 coupled to the drain and source of the silicon semiconductor device. Terminals 1 and 2 are wired through exemplary current sensing resistors analog to digital (A/D) and digital to analog (D/A) circuits 603. Other devices may be used to sense channel current in the field effect devices and still be within the scope of the present invention. Processor 602 stores data and instructions in memory 609. The instructions may be preloaded and contain the steps necessary to implement the various modes of operation for composite field effect device 605 according to embodiments of the present invention. The processor sends data to A/D and D/A unit 603 which is converted to voltage potentials necessary to bias composite field effect device 605 for various operation modes or to reset it after a measurement is made. Power system 608 provides the power supply voltages for the processor 602, memory 609, and A/D and D/A unit 603. Environmental gases 610 are sampled when closure 612 is opened exposing the organic semiconductor channel to the environment.

Although the present invention and its advantages have been described in detail, it should be understood that various changes, substitutions and alterations can be made herein without departing from the spirit and scope of the invention as defined by the appended claims.

What is claimed is:

1. A method of operating an electrical chemical sensing unit using a silicon semiconductor field effect device having an N-type silicon semiconductor channel having a first channel width and extending a first channel length between and electrically coupled to first source and drain terminals, a gate region formed by depositing a gate insulator in alignment with and over the N-type silicon semiconductor channel, an organic semiconductor field effect device having a P-type organic semiconductor channel deposited on the gate region over a portion of the first channel length of the N-type silicon semiconductor channel and extending a second channel length between and electrically coupled to second source and drain terminals, wherein a surface of the organic semiconductor channel is exposed to the ambient environment, and circuitry for selectively applying voltage potentials to at least the first source and drain terminals and the second source and drain terminals in response to program commands comprising, in the following order, the steps of:

a) measuring a first channel current of the N-type silicon semiconductor channel by applying a potential difference between the first source and drain terminals while applying a second voltage potential to the second source and drain terminals;

b) charging the organic semiconductor channel by applying a first positive voltage potential to the second source and drain terminals and the second voltage potential to the first source and drain terminals;

c) measuring a second channel current of the N-type silicon semiconductor channel by applying a third voltage potential between the first source and drain terminals while applying the first positive voltage potential to the second source and drain terminals;

d) applying an analyte to be measured to the surface of the organic semiconductor channel, thereby trapping holes in the organic semiconductor channel by electrostatic coupling;

e) stopping the application of the analyte to the surface of the organic semiconductor channel thus releasing analyte from the surface while retaining some trapped charges;

f) measuring a third channel current of the N-type silicon semiconductor channel by applying the third voltage potential between the first source and drain terminals with no bias applied;

g) calculating the difference between the third and first channel currents as a delta current; and h) correlating the delta current to predetermined measurement data of delta current as a function of analyte concentration.

2. The method of claim 1 further comprising the step of applying a voltage potential to the second source and drain terminals to sweep out the trapped charges caused by step d) thereby resetting the chemical sensing unit.

3. The method of claim 1 wherein the first positive voltage potential is between 4 and 6 volts inclusive.

4. The method of claim 1 wherein the second voltage potential is substantially zero volts.

5. The method of claim 1 further comprising the step of measuring both the organic channel current and the silicon channel current by applying a fourth voltage potential between the second source and drain terminals and the first voltage potential between the first source and drain terminals.

6. The method of claim 5, wherein the fourth voltage potential is in the range of 10 volts, the first voltage potential is in the range of 5 volts, further a voltage potential between the second drain terminal and the first drain terminal is in the range of 20 volts and a voltage potential between the second source terminal and the second source terminal is in the range of 15 volts.

* * * * *